(12) United States Patent
Baumgart et al.

(10) Patent No.: US 9,549,707 B2
(45) Date of Patent: Jan. 24, 2017

(54) SYSTEM FOR ORIENTATION AND DISPLAY OF ULTRASOUND IMAGING DATA

(75) Inventors: John Baumgart, Hoffman Estates, IL (US); Guang Yang, Hoffman Estates, IL (US)

(73) Assignee: SIEMENS MEDICAL SOLUTIONS USA, INC., Malvern, PA (US)

(*) Notice: Subject to any disclaimer, the term of this patent is extended or adjusted under 35 U.S.C. 154(b) by 1079 days.

(21) Appl. No.: 13/532,897

(22) Filed: Jun. 26, 2012

(65) Prior Publication Data

US 2013/0109958 A1 May 2, 2013

Related U.S. Application Data

(60) Provisional application No. 61/554,042, filed on Nov. 1, 2011, provisional application No. 61/554,032, filed on Nov. 1, 2011.

(51) Int. Cl.
| | | |
|---|---|---|
| A61B 8/00 | (2006.01) | |
| A61B 6/12 | (2006.01) | |
| A61B 8/12 | (2006.01) | |
| A61B 6/00 | (2006.01) | |

(52) U.S. Cl.
CPC .............. *A61B 6/12* (2013.01); *A61B 6/425* (2013.01); *A61B 8/12* (2013.01); *A61B 8/4254* (2013.01); *A61B 8/4263* (2013.01); *A61B 8/463* (2013.01)

(58) Field of Classification Search
CPC ......... A61B 6/12; A61B 8/463; A61B 8/4263; A61B 6/425; A61B 8/4254; A61B 8/12

USPC ... 600/407–469; 381/130–131; 382/130–132
See application file for complete search history.

(56) References Cited

U.S. PATENT DOCUMENTS

| | | | | |
|---|---|---|---|---|
| 4,838,879 A | * | 6/1989 | Tanabe et al. | 604/529 |
| 5,345,938 A | * | 9/1994 | Nishiki et al. | 600/463 |
| 5,422,926 A | * | 6/1995 | Smith et al. | 378/121 |
| 6,612,992 B1 | | 9/2003 | Hossack et al. | |
| 7,996,060 B2 | | 8/2011 | Trofimov et al. | |
| 8,057,394 B2 | | 11/2011 | Dala-Krishna | |
| 2006/0079745 A1 | * | 4/2006 | Viswanathan | A61B 5/062 600/407 |
| 2006/0227136 A1 | * | 10/2006 | Boese et al. | 345/424 |
| 2006/0253186 A1 | * | 11/2006 | Bates | 623/1.11 |
| 2007/0038081 A1 | * | 2/2007 | Eck et al. | 600/437 |

(Continued)

OTHER PUBLICATIONS

U.S. Co-pending U.S. Appl. No. 13/532,953, filed Jun. 26, 2012.

*Primary Examiner* — Sanjay Cattungal

(57) ABSTRACT

A system orientates and displays intra-vascular ultrasound imaging data using an acquisition processor and an image data processor. The acquisition processor acquires, during navigation of an ultrasound catheter through a vessel, for multiple individual intra-vascular ultrasound images comprising an image sequence, data representing an individual image and orientation data associated with the individual image indicating orientation of the catheter and individual image with respect to a reference position external to patient anatomy. The image data processor aligns the multiple individual intra-vascular ultrasound images with respect to the external reference position by rotating individual images of the image sequence as necessary to have substantially the same orientation with respect to the external reference position in response to the orientation data.

30 Claims, 7 Drawing Sheets

(56) References Cited

U.S. PATENT DOCUMENTS

| | | |
|---|---|---|
| 2008/0146941 A1* | 6/2008 | Dala-Krishna .......... A61B 8/12 600/466 |
| 2008/0146942 A1* | 6/2008 | Dala-Krishna .......... A61B 6/12 600/466 |
| 2008/0283771 A1* | 11/2008 | Li .......................... A61B 6/463 250/459.1 |
| 2008/0287803 A1* | 11/2008 | Li ........................... A61B 5/06 600/466 |
| 2010/0094125 A1 | 4/2010 | Younge et al. |
| 2011/0021926 A1* | 1/2011 | Spencer ............... A61B 5/0062 600/478 |
| 2011/0238083 A1 | 9/2011 | Moll et al. |
| 2012/0004668 A1 | 1/2012 | Wallace et al. |
| 2012/0113108 A1 | 5/2012 | Dala-Krishna |

* cited by examiner

SYSTEM FOR ORIENTATION AND DISPLAY OF ULTRASOUND IMAGING DATA

This is a non-provisional application of provisional application Ser. No. 61/554,042 filed Nov. 1, 2011, by J. Baumgart et al. and of provisional application Ser. No. 61/554,032 filed Nov. 1, 2011, by J. Baumgart et al.

FIELD OF THE INVENTION

This invention concerns a system for orientation and display of intra-vascular ultrasound imaging data by aligning multiple individual intra-vascular ultrasound images with respect to an external reference position.

BACKGROUND OF THE INVENTION

Intravascular Ultrasound (IVUS) produces a series of tomographic views of a patient vessel as a catheter is pulled through the vessel. However displayed IVUS image data lacks information regarding orientation of the image views with respect to patient anatomy. The display of IVUS image data concurrently with image data showing vessel morphology when the IVUS image data is not oriented to the vessel morphology is often confusing and misleading. A system according to invention principles addresses this deficiency and related problems.

SUMMARY OF THE INVENTION

A system orients IVUS image data to provide a consistent orientation with respect to patient anatomy and an external signal, such as an X-ray pulse or electromagnetic field for showing correctly oriented IVUS image data of patient anatomy co-registered with respect to corresponding angiographic X-ray or CT image data. A system orientates and displays intra-vascular ultrasound imaging data using an acquisition processor and an image data processor. The acquisition processor acquires, during navigation of an ultrasound catheter through a vessel, for multiple individual intra-vascular ultrasound images comprising an image sequence, data representing an individual image and orientation data associated with the individual image indicating orientation of the catheter and individual image with respect to a reference position external to patient anatomy. The image data processor aligns the multiple individual intra-vascular ultrasound images with respect to the external reference position by rotating individual images of the image sequence as necessary to have substantially the same orientation with respect to the external reference position in response to the orientation data.

DETAILED DESCRIPTION OF THE INVENTION

Figure 1:
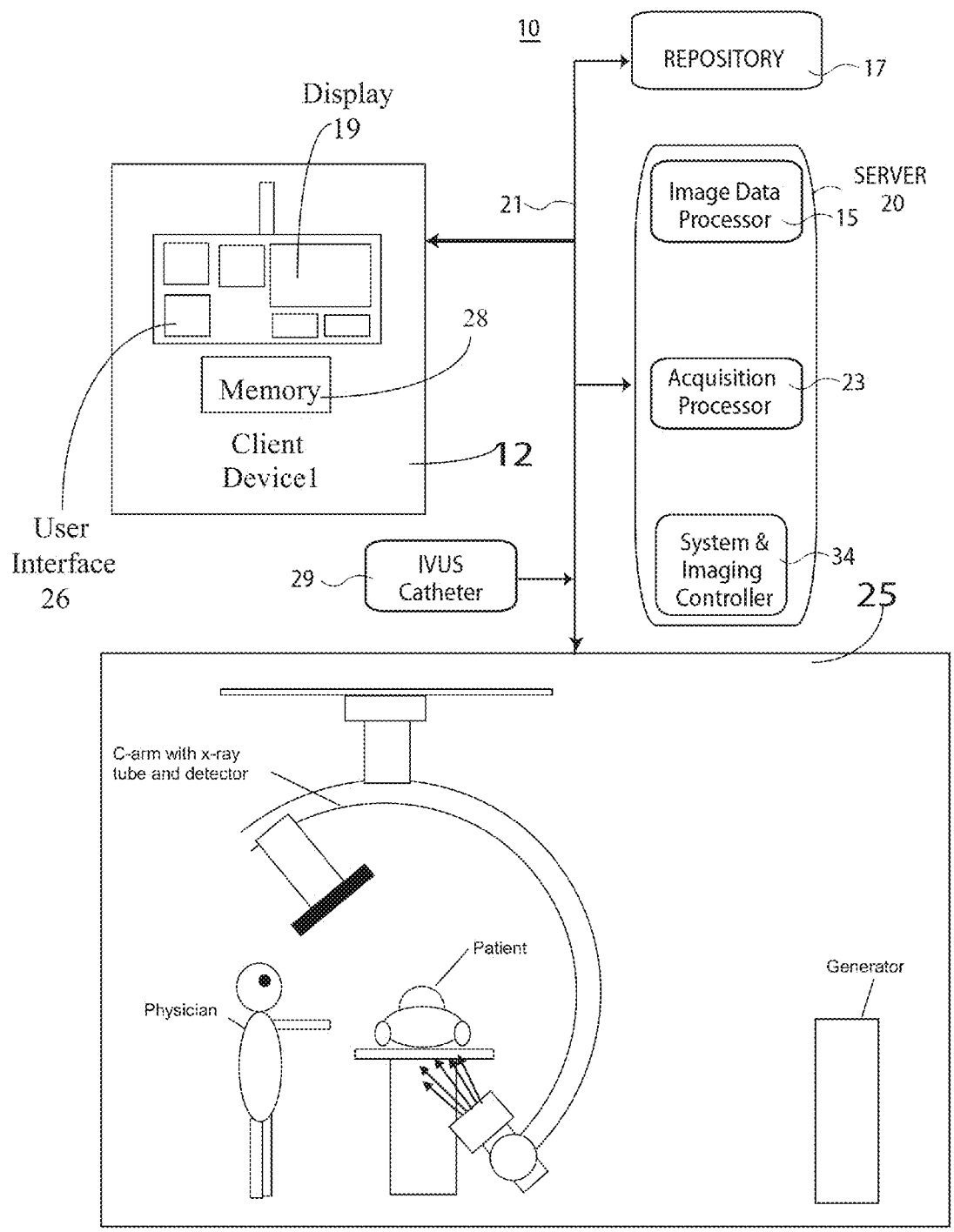
FIG. 1 shows a system for orientation and display of intra-vascular ultrasound imaging data, according to invention principles.

A system orients Intravascular Ultrasound (IVUS) data to provide a consistent orientation with respect to patient anatomy and an external signal, such as an X-ray pulse or electromagnetic field. Oriented IVUS image data is co-registered with angiographic X-ray or CT image data that shows patient anatomy in known orientation. The system advantageously correlates orientation data with IVUS images used for display. The orientation is derived from one or more different sources, including, for example, orientation detected by an IVUS catheter during catheter pullback and orientation detected by analysis of X-ray frames acquired during the pullback FIG. 1 shows system 10 for orientation and display of intra-vascular ultrasound imaging data. System 10 includes one or more processing devices (e.g., workstations, computers or portable devices such as notebooks, Personal Digital Assistants, phones) 12 that individually include memory 28, a user interface 26 enabling user interaction with a Graphical User Interface (GUI) and display 19 supporting GUI and medical image presentation in response to predetermined user (e.g., physician) specific preferences. System 10 also includes at least one repository 17, server 20, IVUS catheter 29 and imaging device 25. Server 20 includes image data processor 15, acquisition processor 23 and system and imaging control unit 34. System and imaging control unit 34 controls operation of one or more imaging devices 25 for performing image acquisition of patient anatomy in response to user command. Imaging devices 25 may comprise a mono-plane or biplane X-ray imaging system. The units of system 10 intercommunicate via network 21. At least one repository 17 stores X-ray and IVUS medical images and studies for patients in DICOM compatible (or other) data format. A medical image study individually includes multiple image series of a patient anatomical portion which in turn individually include multiple images.

Acquisition processor 23 acquires, during navigation of an ultrasound catheter 29 through a vessel, for multiple individual intra-vascular ultrasound images comprising an image sequence, data representing an individual image and orientation data associated with the individual image indicating orientation of the catheter and individual image with respect to a reference position external to patient anatomy. Image data processor 15 aligns the multiple individual intra-vascular ultrasound images with respect to the external reference position by rotating individual images of the image sequence as necessary to have substantially the same orientation with respect to the external reference position in response to the orientation data.

In one embodiment, IVUS catheter 29 detects its orientation with respect to a patient by detecting a direction of an external signal source comprising an X-ray radiation source in X-ray imaging system 25. Catheter 29 in one embodiment, advantageously employs a ring-like array of X-ray microdetectors arranged around the catheter 29 circumference. The catheter determines direction by sensing X-ray (or other radiation) signal strength in a direction of each microdetector and interpolates the direction of the X-ray signal and source from this data. In another embodiment, orientation of IVUS catheter 29 is determined from X-ray images using an IVUS catheter advantageously including a radio-opaque marker occurring around the circumference and varying around the circumference enabling determination of catheter orientation by presenting a unique 2-dimensional X-ray profile at different catheter rotational angle. Image data processor 15 determines orientation using this profile. The orientation data indicates an angle, γ, between the "top" of the IVUS image, determined independently of orientation, and a direction identified by an external signal. For display of tomographic slices, this angle is used to either automatically rotate the IVUS images to match the vascular morphology as seen from an external view, such as in an angiographic X-ray, or to automatically indicate on the IVUS image the direction of the signal source.

Figure 2:
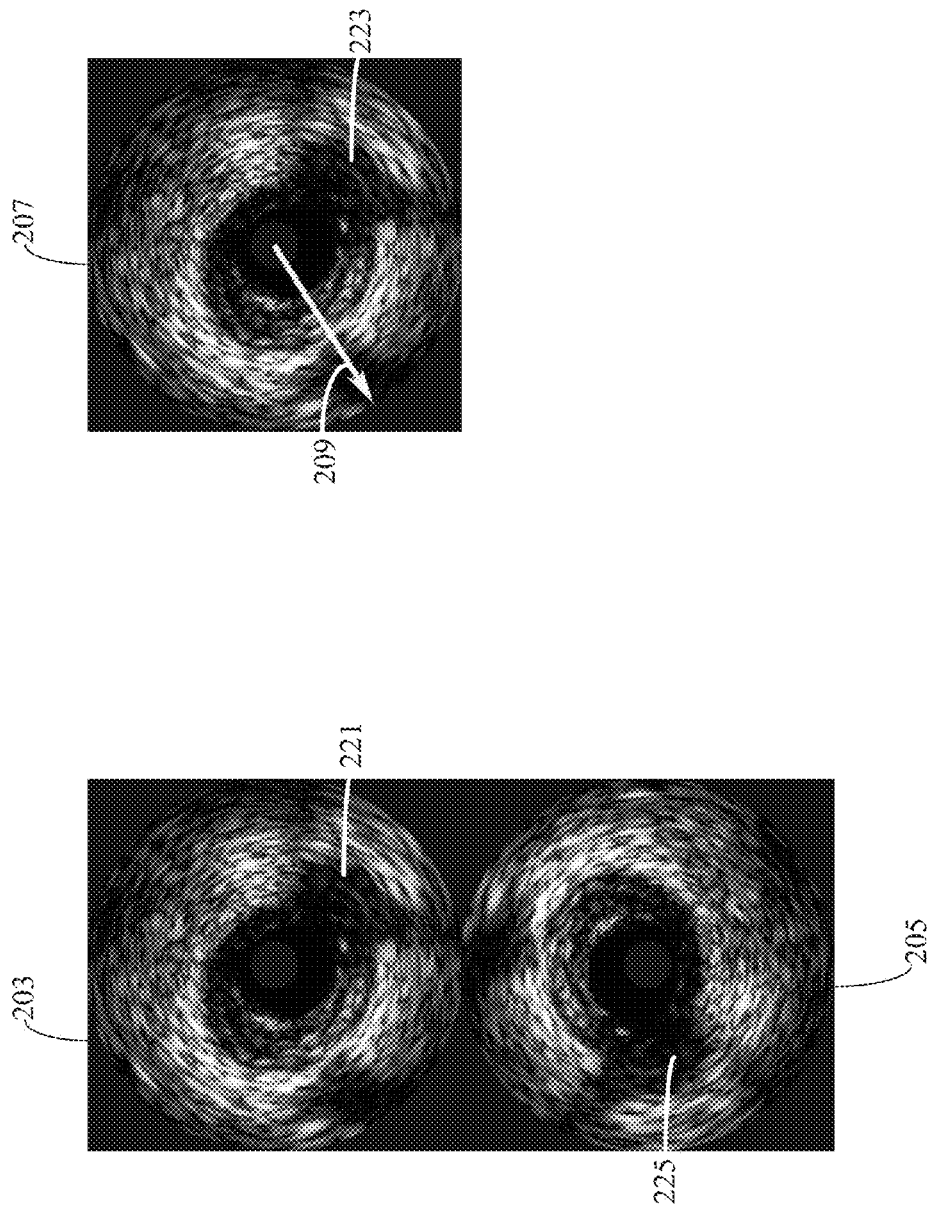
FIG. 2 shows non-oriented IVUS images and an oriented IVUS image, according to invention principles.

FIG. 2 shows non-oriented IVUS images 203, 205 and an oriented IVUS image 207 provided by IVUS catheter 29. Image data processor 15 provides IVUS image 207 advantageously including additional indicator 209 showing a detected direction of an external signal. IVUS image 207 is rotated to keep an external point of view at the top of the image. In images 203 207, dark areas 221, 223 respectively and area 225 in image 205 in the peripheral part of the IVUS image data indicate a vessel branching off the vessel. A longitudinal view of the IVUS image data set is formed by stacking the series of tomographic views and taking a slice through the image stack. The result provides an improved view of vessel branches off the vessel being imaged by IVUS catheter 29, but as it is comprised of non-oriented slices, it does not correspond to an angiographic view of the same vessel.

Figure 3:
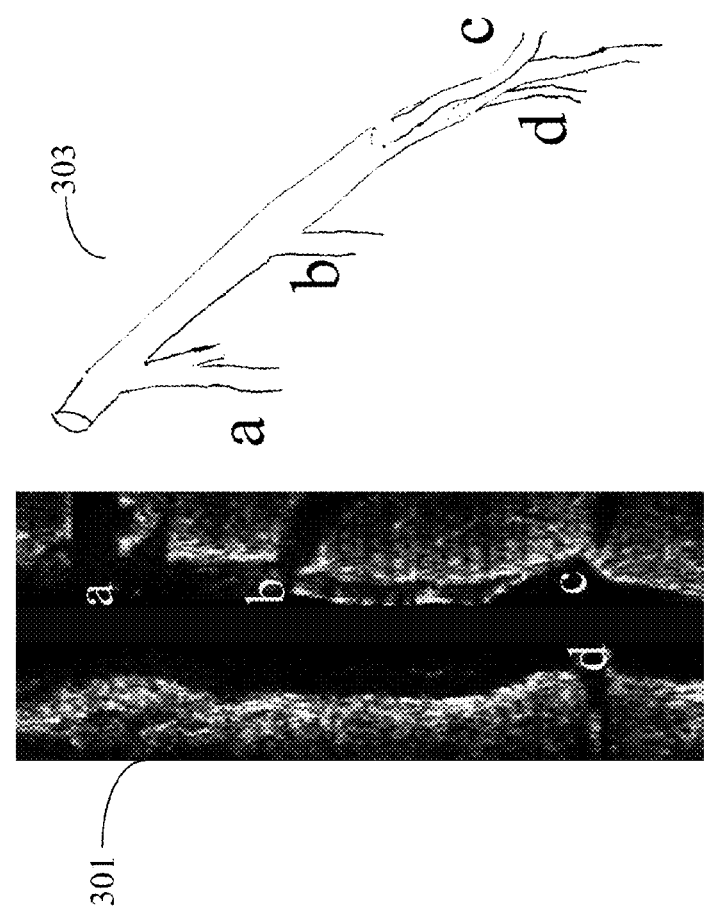
FIG. 3 shows a longitudinal view of IVUS acquisition and an angiographic view of the same vessel, according to invention principles.

FIG. 3 shows longitudinal view 301 of an IVUS acquisition and angiographic view 303 of the same vessel. Views 301 and 303 show vessels a, b, c branching off the main vessel on the right side of longitudinal view 303, and vessel d on the left side. Angiogram view 303 shows how these vessels may be seen differently in the presence of rotation of the IVUS transducer with respect to the imaging source. Vessels a and b branch to the right in longitudinal IVUS image 301 and to the left in angiographic view 303. However, branches c and d are seen at right and left in both IVUS image 301 and 2-dimensional angiographic projection image 303. Angiographic view 303 fails to reveal that vessel c branches from the front of the vessel toward the viewer before continuing to the right, and vessel d branches from the rear, overlapping the main vessel before continuing to the left. Image data processor 15 corrects orientation of the individual IVUS image slices comprising longitudinal view 301 so that view 301 more closely represents angiographic view 303.

Figure 4:
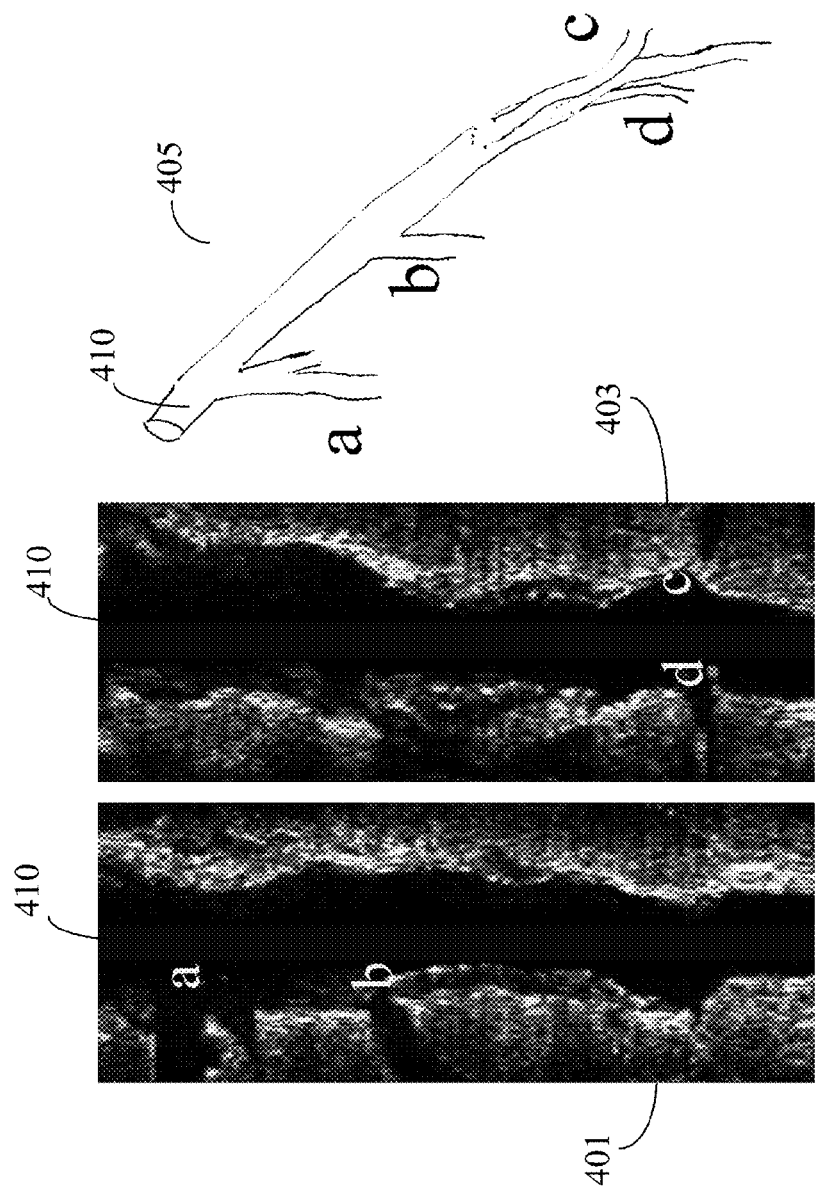
FIG. 4 shows longitudinal views oriented to the point of view of the angiographic projection showing vessels a and b, and a view rotated 90 degrees around the main vessel showing vessels c and d, according to invention principles.

FIG. 4 shows longitudinal views 401, 403 oriented to the point of view of the angiographic projection image 405. Specifically, IVUS image 401 and angiogram, image 405 show vessels a and b. IVUS image 405 shows vessels c and d in a view rotated 90 degrees around main vessel 410. Longitudinal tomographic image slice 401 and reoriented tomographic slice 403 correspond to locations of the branches shown in angiographic projection image 405.

Figure 5:
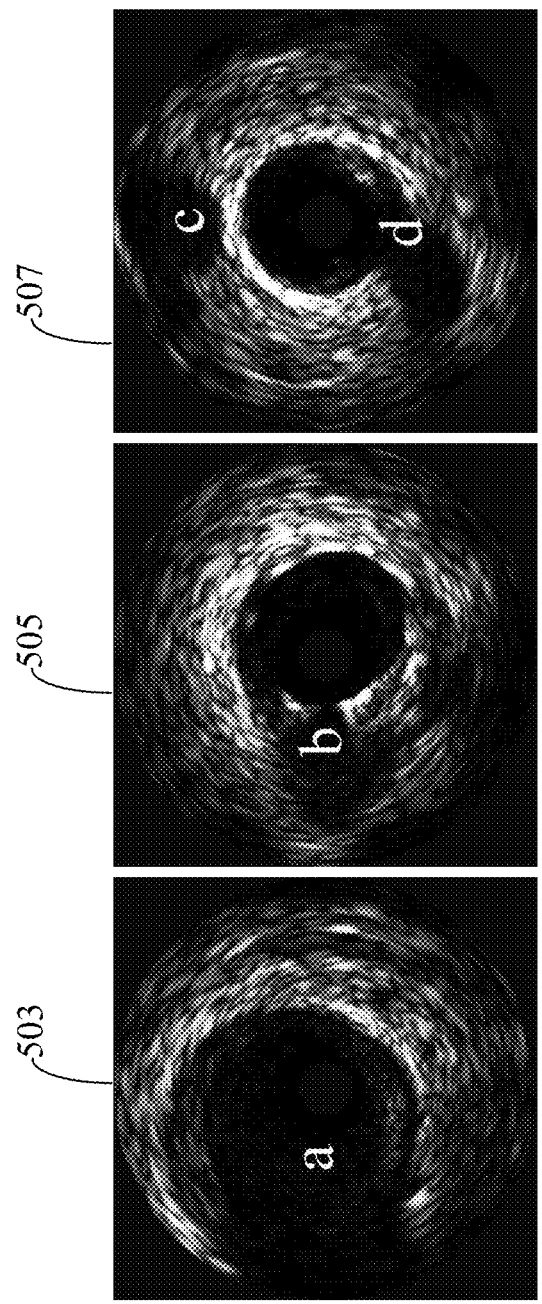
FIG. 5 shows tomographic IVUS image slices showing branches of a vessel reoriented to match the orientation of the vessel as seen in an angiographic projection image, according to invention principles.

FIG. 5 shows tomographic IVUS image slices showing branches of a vessel reoriented to match the orientation of the vessel as seen in an angiographic projection image. Image slices 503 and 505 show vessel branches a and b respectively, have been rotated by 180° to show the branches on the left in order to match an angiographic view. Image slice 507 shows branches c and d have been rotated 90° to show the branches coming off the front and back of the main vessel.

System 10 produces an IVUS image display oriented to a particular point of view. In one embodiment, the system acquire IVUS image data and data identifying orientation of IVUS catheter 29 with respect to a constant point of reference by reading this information directly from IVUS catheter 29 at the time of the IVUS image data acquisition. In another embodiment, the system acquire IVUS image data and data identifying orientation of IVUS catheter 29 with respect to a constant point of reference by discerning the orientation from a dataset temporally correlated with the IVUS image data, such as X-ray images at the time of the IVUS image data acquisition. System 10 generates a reoriented group of tomographic IVUS images by rotating each individual image according to a determined orientation angle, γ, corresponding to the individual image or interpolated from known orientation angles of nearby images.

Image data processor 15 constructs a longitudinal vessel view from the reoriented IVUS slices and presents the reoriented IVUS longitudinal data view on display 19. The displayed IVUS reoriented tomographic data is configurable to indicate a direction of an external point of view which may move from frame to frame. Image data processor 15 presents on display 19 the original tomographic data before reorientation and indicates the direction of the external point of view which may move from frame to frame.

Figure 6:
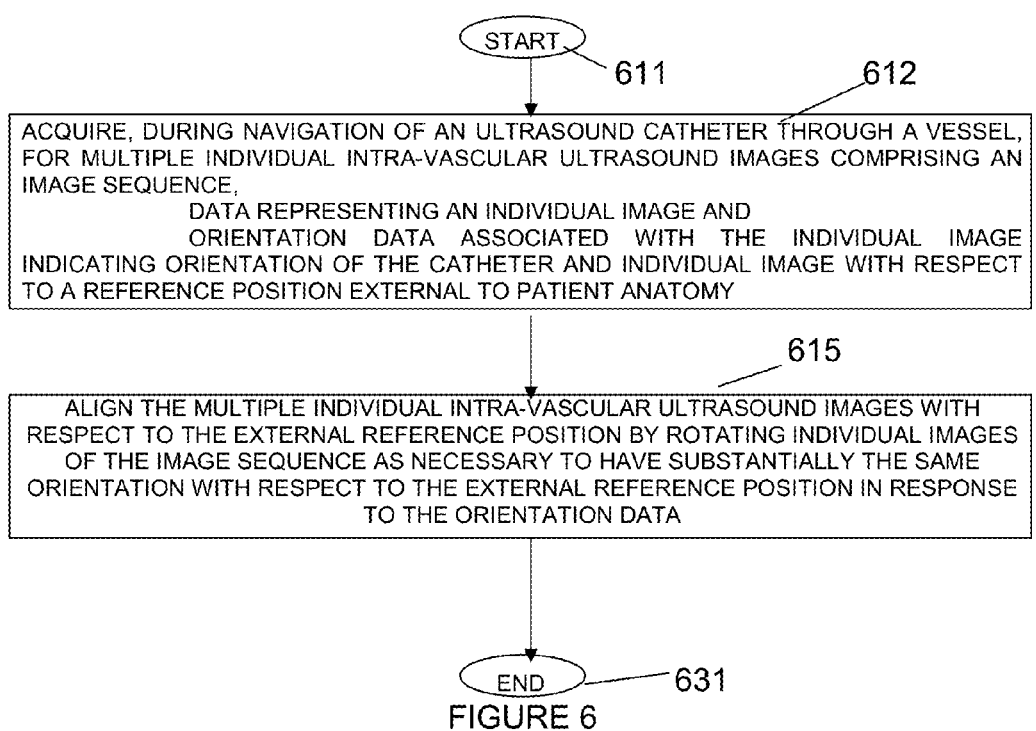
FIG. 6 shows a flowchart of a process employed by a system for orientation and display of intra-vascular ultrasound imaging data, according to invention principles.

FIG. 6 shows a flowchart of a process employed by system 10 (FIG. 1) for orientation and display of intra-vascular ultrasound imaging data. Acquisition processor 23 in step 612 following the start at step 611 acquires, during navigation of an ultrasound catheter through a vessel, for multiple individual intra-vascular ultrasound images comprising an image sequence, data representing an individual image and orientation data associated with the individual image indicating orientation of both the catheter and the individual image with respect to a reference position external to patient anatomy. The external reference position is a position of a source of electro-magnetic radiation such as an X-ray radiation source in an X-ray imaging system, a direction indicating reference point, or an X-ray radiation detector plane, for example. The orientation data associated with the individual image indicates angular rotation of the catheter and individual image with respect to a reference image in the image sequence. The orientation data also indicates angular rotation of the catheter with respect to the source and is derived from analysis of an X-ray image acquired of the vessel and ultrasound catheter corresponding to the individual image and acquired at substantially the same time as the individual image. In one embodiment, the orientation data is derived from signal data acquired from a radiation detector array around the circumference of the ultrasound catheter. The signal data indicates X-ray signal strength in a direction of an individual detector of the array. Image data processor 15 processes the signal data to determine orientation of the catheter with respect to the source by interpolating the direction of the X-ray source from X-ray signal strength detected in each direction of each individual detector of the array.

In one embodiment, the angular rotation of the catheter is derived from analysis of first and second X-ray images acquired of the vessel corresponding to the reference image and individual intravascular ultrasound image, respectively and acquired at substantially the same times. The analysis of first and second X-ray images determines the angular rotation by determining rotational movement of a feature on the catheter between the first and second X-ray images. In one embodiment, the angular rotation of the catheter with respect to the source is derived from analysis of the X-ray image in response to a radio-opaque marker around the circumference of the catheter comprising a 2-dimensional X-ray profile uniquely identifying angular rotation of the catheter in the image. In step 615 image data processor 15 aligns the multiple individual intra-vascular ultrasound images with respect to the external reference position by rotating individual images of the image sequence as necessary to have substantially the same orientation with respect to the external reference position in response to the orientation data. The process of FIG. 6 terminates at step 631.

Figure 7:
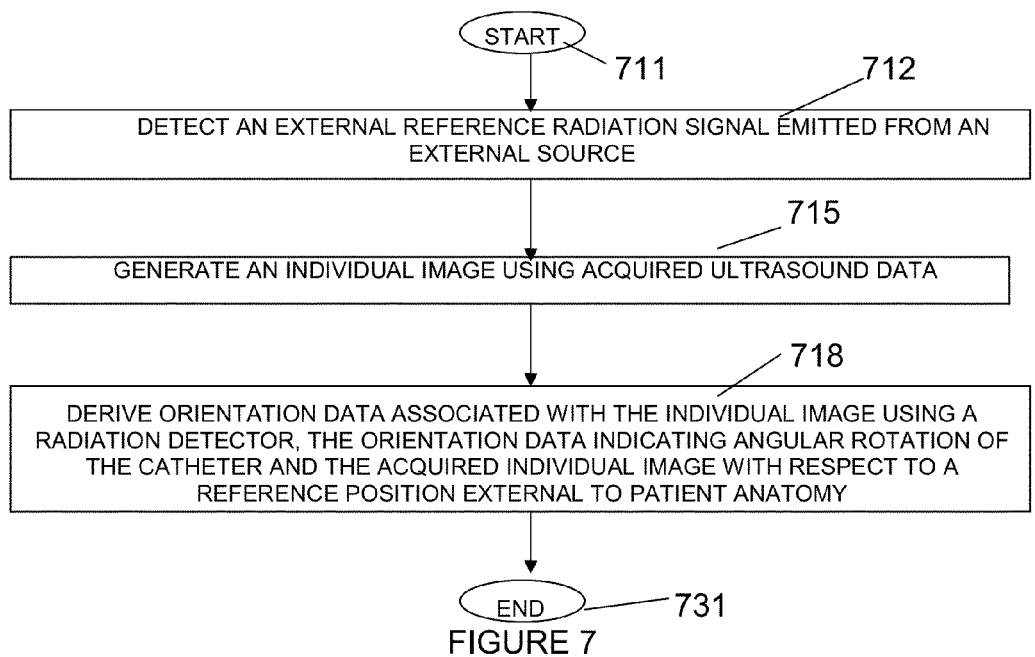
FIG. 7 shows a flowchart of a process employed by an ultrasound catheter supporting orientation and display of intra-vascular ultrasound imaging data, according to invention principles.

FIG. 7 shows a flowchart of a process employed by ultrasound catheter 29 and system 10 (FIG. 1) supporting orientation and display of intra-vascular ultrasound imaging data. The system in step 712 following the start at step 711, detects an external reference radiation signal emitted from an external source and in step 715 generates an individual image using acquired ultrasound data. The external reference radiation signal comprises an X-ray radiation signal. In step 718 the system derives orientation data associated with the individual image using a radiation detector. The orientation data indicates angular rotation of the catheter and the acquired individual image with respect to a reference position external to patient anatomy. In one embodiment, the orientation data associated with the individual image indicates angular rotation of the catheter with respect to the source and is derived from analysis of an X-ray image acquired of the catheter within a vessel corresponding to the acquired individual image and acquired at substantially the same time as the acquired individual image.

In an embodiment, a radiation detector array of individual radiation detectors provides signal data indicating X-ray signal strength in a direction of each detector. Image data processor 15 processes the signal data indicating X-ray signal strength, to determine orientation of the catheter with respect to the source by interpolating the direction of the X-ray source from X-ray signal strength detected in each direction of each detector. The angular rotation of the catheter with respect to the source is derived from analysis of the X-ray image in response to a radio-opaque marker around the circumference of the catheter comprising a 2-dimensional X-ray profile uniquely identifying angular rotation of the catheter in the image. The external reference position is a position of a radiation signal source of an X-ray imaging method. The process of FIG. 7 terminates at step 731.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication there-between. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of the FIGS. 1-7 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system orients IVUS data to provide a consistent orientation with respect to patient anatomy and an external signal, such as an X-ray pulse or electromagnetic field for showing correctly oriented IVUS image data of patient anatomy with respect to corresponding angiographic X-ray or CT image data. Further, the processes and applications may, in alternative embodiments, be located on one or more (e.g., distributed) processing devices on a network linking the units of FIG. 1. Any of the functions and steps provided in FIGS. 1-7 may be implemented in hardware, software or a combination of both. No claim element herein is to be construed under the provisions of 35 U.S.C. 112, sixth paragraph, unless the element is expressly recited using the phrase "means for."

What is claimed is:

1. A system for orientation and display of intra-vascular ultrasound imaging data, comprising:
   an acquisition processor configured for acquiring, during navigation of an ultrasound catheter through a vessel, for a plurality of individual intra-vascular ultrasound images comprising an image sequence,
      data representing an individual image and
      orientation data associated with said individual image indicating orientation of said catheter and individual image with respect to a reference position;
   an image data processor for generating a plurality of reoriented individual intra-vascular ultrasound images, wherein the individual intra-vascular ultrasound images are reoriented by aligning said plurality of individual intra-vascular ultrasound images with respect to the reference position by rotating individual images of said image sequence to have substantially the same orientation with respect to said reference position in response to said orientation data; and
   a display for displaying the reoriented individual intra-vascular ultrasound images, wherein the image data processor presents on the display the original data before reorientation and indicates the direction of the reference position.

2. The system according to claim 1, wherein
   the reference position is external to patient anatomy,
   the external reference position is a position of an X-ray radiation source in an X-ray imaging system and
   said orientation data associated with said individual image indicates angular rotation of said catheter and individual image with respect to a reference image in said image sequence.

3. The system according to claim 2, wherein
   said angular rotation of said catheter is derived from analysis of first and second X-ray images acquired of said vessel corresponding to said reference image and individual intravascular ultrasound image, respectively and acquired at substantially the same times.

4. The system according to claim 3, wherein
   said analysis of first and second X-ray images determines said angular rotation by determining rotational movement of a feature on said catheter between said first and second X-ray images.

5. The system according to claim 1, wherein
   said reference position is a position of a source of electromagnetic radiation.

6. The system according to claim 1, wherein
   said reference position is a position of a radiation signal source and
   said orientation data associated with said individual image indicates angular rotation of said catheter with respect to said source and is derived from analysis of an X-ray image acquired of said vessel and ultrasound catheter corresponding to said individual image and acquired at substantially the same time as said individual image.

7. The system according to claim 6, wherein
   said angular rotation of said catheter with respect to said source is derived from analysis of said X-ray image in response to a radio-opaque marker around the circumference of the catheter comprising a 2-dimensional X-ray profile uniquely identifying angular rotation of the catheter in said image.

8. The system according to claim 1, wherein
   said reference position is a position of a radiation signal source and
   said orientation data associated with said individual image indicates angular rotation of said catheter with respect to said source and is derived from signal data acquired from a radiation detector array around the circumference of said ultrasound catheter.

9. The system according to claim 8, wherein
   said radiation detector array comprises an array of individual radiation microdetectors and said signal data indicates X-ray signal strength in a direction of each microdetector and
   said image data processor processes said signal data to determine orientation of said catheter with respect to said source by interpolating the direction of the X-ray source from X-ray signal strength detected in each direction of each microdetector.

10. The system according to claim 1, wherein
    said reference position is a direction indicating reference point.

11. The system according to claim 1, wherein
    said reference position is an X-ray radiation detector plane.

12. An ultrasound catheter system supporting orientation and display of intra-vascular ultrasound imaging data, comprising:
    an external reference radiation signal source configured to be positioned external to a patient anatomy and an ultrasound catheter including a radiation detector configured for providing,
       an individual image acquired using the ultrasound catheter, and
       orientation data associated with said individual image and derived using the radiation detector, said orientation data indicating angular rotation of said catheter in a vessel and the acquired individual image with respect to a reference position external to patient anatomy, wherein the radiation detector detects an orientation of the catheter with respect to the patient anatomy by detecting a direction of the reference radiation signal source,
    wherein said external reference position is a position of a radiation signal source of an X-ray imaging system and said orientation data associated with said individual image indicates angular rotation of said catheter with respect to said source and is derived from analysis of an X-ray image acquired by said imaging system of an ultrasound catheter within a vessel corresponding to said acquired individual image and acquired at substantially the same time as said acquired individual image.

13. The system according to claim 12, wherein
    said external reference radiation signal source comprises an X-ray radiation source of an X-ray imaging system and
    said radiation detector comprises a radiation detector array of individual radiation microdetectors and provides signal data indicates X-ray signal strength in a direction of each microdetector enabling an image data processor to process said signal data to determine orientation of said catheter with respect to said source by interpolating the direction of the X-ray source from X-ray signal strength detected in each direction of each microdetector.

14. The system according to claim 12, wherein
said angular rotation of said catheter with respect to said source is derived from analysis of said X-ray image in response to a radio-opaque marker around the circumference of the catheter comprising a 2-dimensional X-ray profile uniquely identifying angular rotation of the catheter in said image.

15. A method for orientation and display of intra-vascular ultrasound imaging data, comprising the activities of:
acquiring, during navigation of an ultrasound catheter through a vessel, for a plurality of individual intra-vascular ultrasound images comprising an image sequence,
data representing an individual image and
orientation data associated with said individual image indicating orientation of said catheter and individual image with respect to a reference position external to patient anatomy;
generating a plurality of reoriented individual intra-vascular ultrasound images, wherein the individual intra-vascular ultrasound images are reoriented by aligning said plurality of individual intra-vascular ultrasound images with respect to the external reference position by rotating individual images of said image sequence to have substantially the same orientation with respect to said external reference position in response to said orientation data; and
displaying the reoriented individual intra-vascular ultrasound images and the original data before reorientation with indication of the direction of the reference position.

16. The method according to claim 15, wherein
said external reference position is a position of an X-ray radiation source in an X-ray imaging system and
said orientation data associated with said individual image indicates angular rotation of said catheter and individual image with respect to a reference image in said image sequence.

17. The method according to claim 16, wherein
said angular rotation of said catheter is derived from analysis of first and second X-ray images acquired of said vessel corresponding to said reference image and individual intravascular ultrasound image, respectively and acquired at substantially the same times.

18. The method according to claim 17, wherein
said analysis of first and second X-ray images determines said angular rotation by determining rotational movement of a feature on said catheter between said first and second X-ray images.

19. The method according to claim 15, wherein
said external reference position is a position of a source of electro-magnetic radiation.

20. The method according to claim 15, wherein
said external reference position is a position of a radiation signal source and
said orientation data associated with said individual image indicates angular rotation of said catheter with respect to said source and is derived from analysis of an X-ray image acquired of said vessel and ultrasound catheter corresponding to said individual image and acquired at substantially the same time as said individual image.

21. The method according to claim 20, wherein
said angular rotation of said catheter with respect to said source is derived from analysis of said X-ray image in response to a radio-opaque marker around the circumference of the catheter comprising a 2-dimensional X-ray profile uniquely identifying angular rotation of the catheter in said image.

22. The method according to claim 15, wherein
said external reference position is a position of a radiation signal source and
said orientation data associated with said individual image indicates angular rotation of said catheter with respect to said source and is derived from signal data acquired from a radiation detector array around the circumference of said ultrasound catheter.

23. The method according to claim 22, wherein
said signal data indicates X-ray signal strength in a direction of an individual detector of said array and including the step of
processing said signal data to determine orientation of said catheter with respect to said source by interpolating the direction of the X-ray source from X-ray signal strength detected in each direction of each individual detector of said array.

24. A method used by an ultrasound catheter supporting orientation and display of intra-vascular ultrasound imaging data, comprising the activities of:
detecting an external reference radiation signal emitted from a source external to a patient anatomy;
generating an individual image using acquired ultrasound data;
detecting with a radiation detector a direction of the external reference radiation signal source to detect an orientation of the catheter with respect to the patient anatomy; and
deriving orientation data associated with said individual image using the radiation detector, said orientation data indicating angular rotation of said catheter and the acquired individual image with respect to a reference position,
wherein said orientation data associated with said individual image indicates angular rotation of said catheter with respect to said source and is derived from analysis of an X-ray image acquired of said catheter within a vessel corresponding to said acquired individual image and acquired at substantially the same time as said acquired individual image.

25. The method according to claim 24, wherein
said external reference radiation signal comprises an X-ray radiation signal and including the steps of
using a radiation detector array of individual radiation detectors providing signal data indicating X-ray signal strength in a direction of each detector and
processing said signal data indicating X-ray signal strength, to determine orientation of a catheter with respect to said source by interpolating the direction of the X-ray source from X-ray signal strength detected in each direction of each detector.

26. The method according to claim 24, wherein
said angular rotation of said catheter with respect to said source is derived from analysis of said X-ray image in response to a radio-opaque marker around the circumference of the catheter comprising a 2-dimensional X-ray profile uniquely identifying angular rotation of the catheter in said image.

27. A system for orientation and display of intra-vascular ultrasound imaging data, comprising:
an acquisition processor configured for acquiring, during navigation of an ultrasound catheter through a vessel, for a plurality of individual intra-vascular ultrasound images comprising an image sequence,
data representing an individual image and
orientation data associated with said individual image indicating orientation of said catheter and individual image with respect to a reference position, wherein said reference position is a position of a radiation signal source;
an image data processor for aligning said plurality of individual intra-vascular ultrasound images with respect to the reference position by rotating individual images of said image sequence to have substantially the same orientation with respect to said reference position in response to said orientation data;
wherein said orientation data associated with said individual image indicates angular rotation of said catheter with respect to said source and is derived from signal data acquired from a radiation detector array around the circumference of said ultrasound catheter;
wherein said radiation detector array comprises an array of individual radiation microdetectors and said signal data indicates X-ray signal strength in a direction of each microdetector;
wherein said image data processor processes said signal data to determine orientation of said catheter with respect to said source by interpolating the direction of the X-ray source from X-ray signal strength detected in each direction of each microdetector; and
a display for displaying the reoriented individual intra-vascular ultrasound images.

28. An ultrasound catheter system supporting orientation and display of intra-vascular ultrasound imaging data, comprising:
an external reference radiation signal source comprising an X-ray radiation source of an X-ray imaging system and
an ultrasound catheter including a radiation detector configured for providing,
an individual image acquired using the ultrasound catheter, and
orientation data associated with said individual image and derived using the radiation detector, said orientation data indicating angular rotation of said catheter and the acquired individual image with respect to a reference position external to patient anatomy; and
wherein said radiation detector comprises a radiation detector array of individual radiation microdetectors and provides signal data indicates X-ray signal strength in a direction of each microdetector enabling an image data processor to process said signal data to determine orientation of said catheter with respect to said source by interpolating the direction of the X-ray source from X-ray signal strength detected in each direction of each microdetector.

29. A method for orientation and display of intra-vascular ultrasound imaging data, comprising the activities of:
acquiring, during navigation of an ultrasound catheter through a vessel, for a plurality of individual intra-vascular ultrasound images comprising an image sequence,
data representing an individual image and
orientation data associated with said individual image indicating orientation of said catheter and individual image with respect to a reference position external to patient anatomy, wherein said external reference position is a position of a radiation signal source; and
aligning said plurality of individual intra-vascular ultrasound images with respect to the external reference position by rotating individual images of said image sequence to have substantially the same orientation with respect to said external reference position in response to said orientation data;
wherein said orientation data associated with said individual image indicates angular rotation of said catheter with respect to said source and is derived from signal data acquired from a radiation detector array around the circumference of said ultrasound catheter; and
wherein said signal data indicates X-ray signal strength in a direction of an individual detector of said array and including the step of processing said signal data to determine orientation of said catheter with respect to said source by interpolating the direction of the X-ray source from X-ray signal strength detected in each direction of each individual detector of said array; and
displaying the reoriented individual intra-vascular ultrasound images.

30. A method used by an ultrasound catheter supporting orientation and display of intra-vascular ultrasound imaging data, comprising the activities of:
detecting an external reference radiation signal emitted from an external source, wherein said external reference radiation signal comprises an X-ray radiation signal;
generating an individual image using acquired ultrasound data;
deriving orientation data associated with said individual image using a radiation detector, said orientation data indicating angular rotation of said catheter and the acquired individual image with respect to a reference position;
using a radiation detector array of individual radiation detectors providing signal data indicating X-ray signal strength in a direction of each detector; and
processing said signal data indicating X-ray signal strength, to determine orientation of a catheter with respect to said source by interpolating the direction of the X-ray source from X-ray signal strength detected in each direction of each detector.

* * * * *